US006521430B1

(12) United States Patent
Orwar et al.

(10) Patent No.: US 6,521,430 B1
(45) Date of Patent: Feb. 18, 2003

(54) METHOD FOR ELECTRO-PERMEABILIZATION OF INDIVIDUAL CELLULAR AND ORGANELLAR STRUCTURES AND USE THEREOF

(75) Inventors: Owe Orwar, Göteborg (SE); Anders Lundqvist, Göteborg (SE); Peter Eriksson, Göteborg (SE); Daniel Chiu, Newark, CA (US)

(73) Assignee: Cellectricon AB, Gothenburg (SE)

( * ) Notice: Subject to any disclaimer, the term of this patent is extended or adjusted under 35 U.S.C. 154(b) by 0 days.

(21) Appl. No.: 09/557,979

(22) Filed: Apr. 25, 2000

Related U.S. Application Data

(63) Continuation of application No. PCT/SE98/02012, filed on Nov. 6, 1998.

(30) Foreign Application Priority Data

Nov. 6, 1997 (SE) ............................................... 9704076

(51) Int. Cl.[7] ........................ C12N 13/00; C12N 15/87; A61B 5/04

(52) U.S. Cl. .................... 435/173.6; 435/461; 600/373; 600/377; 600/378; 600/381; 600/395

(58) Field of Search ................................. 435/461, 207, 435/173.6, 173.5; 600/372, 373, 309, 377, 378, 381, 395; 436/149; 604/20

(56) References Cited

U.S. PATENT DOCUMENTS

| | | | | |
|---|---|---|---|---|
| 5,019,034 A | * | 5/1991 | Weaver et al. ................. | 604/20 |
| 5,137,817 A | * | 8/1992 | Busta et al. | |
| 5,389,069 A | | 2/1995 | Weaver | |
| 5,501,662 A | | 3/1996 | Hofmann | |
| 5,702,359 A | | 12/1997 | Hofmann et al. | |

FOREIGN PATENT DOCUMENTS

| | | | |
|---|---|---|---|
| DE | WO 97/05922 | * | 2/1997 |
| WO | WO 96/39226 | | 12/1996 |

OTHER PUBLICATIONS

Needham, Measurement of interbilayer adhesion energies, 1993, Methods in Enzymology, vol. 220, pp. 111–129.*

"Altering the Biochemical State of Individual Cultured Cells and Organelles with Ultramicroclectrodes", J. Anders Lundqvist et al., *Proc. Natl. Acad. Sci. USA*, vol. 95 (Sep. 1998) pp. 10356–10360.

"Kinetics of Release of Serotonin from Isolated Secretory Granules, I. Amperometric Detection of Serotonin from Electroporated Granules", P. E. Marszalek et al., *Biophysical Journal*, vol. 73 (Sep. 1997) pp. 1160–1168.

Ryttsén, Frida et al., "*Characterization of Single–Cell Electroporation by Using Patch–Clamp and Fluorescence Microscopy*", 79 Biophysical Journal 1993–2001 (2000).

Åberg, Maria A.I., et al., "*Selective Introduction of Antisense Oligonucleotides into Single Adult CNS Progenitor Cells Using Electroporation Demonstrates the Requirement of Stat3 Activation for CNTF–Induced Gliogenesis*", 17 Molecular and Cellular Neuroscience 426–443 (2001).

Nolkrantz, Kerstin et al., "*Electroporation of Single Cells and Tissues with an Electrolyte–filled Capillary*", 73 Anal. Chem. 4469–4477 (2001).

Lundqvist, Anders J., et al., "*Altering the biochemical state of individual cultured cells and organelles with ultramicroelectrodes*", 95 Proc. Natl. Acad. Sci. 10356–10360 (1998).

Jorgenson, James W. et al., "*Zone electrophoresis in Open–Tubular Glass Capillaries*", 53 Anal. Chem. 1298–1302 (1981).

O. P. Hamill, A. Marty, E. Heher, B. Sakman, F. J. Sigworth, *Pfleugers Arch.* 391, 85–100 (1981).

S. Maiti, J. B. Shear, R. M. Williams, W. R Zipfel, W. W. Webb, *Science,* 275, 530–532 (1997).

R. H. Chow, L. von Ruden, E. Neher, *Nature,* 356, 60–63 (1992).

R. M. Wightman, J.A. Jankowski, R. T. Kennedy, K. T. Kawagoe, T. J. Scroeder, D. J. Leszczyszyn, J.A. Near, E. J. Diliberto Jr., O. H. Viveros, *Proc. Natl. Acad. Sic. U.S.A.,* 88, 10754–10758 (1991).

M.R. Capecchi, *Cell,* 22, 479–488 (1980).

Zimmermann, U. *Biochim. Biophys Acta,* 694, 227–277 (1982).

Tsong, T. Y. *Biophys. J.,* 60, 297–306 (1991).

Weaver, J. C. *J. Cell. Biochem.,* 51, 426–435 (1993).

J–M. Collombet, V.C. Wheeler, F. Vogel, & C. Coutelle *J. Biol. Chem.,* 272, 5342–5347 (1997).

K. Kinosita, K., Jr., I. Ashikawa, N. Saita, H. Yoshimura, H. Itoh, K. Nagayama, & A. Ikegami *J. Biophys.,* 53, 1015–1019 (1988).

M. Hibino, M. Shigemori, H. Itoh, K. Nagayama, & K. Kinosita, K., Jr., *biophys. J.,* 59, 209–220 (1991).

(List continued on next page.)

Primary Examiner—James Ketter
Assistant Examiner—Konstantina Katcheves
(74) Attorney, Agent, or Firm—David C. Conlin; Dianne M. Rees; Edward & Angell, LLP

(57) ABSTRACT

The invention relates to a method for permeabilization of a cell structure consisting of a single cell, an intracellular structure or an organelle comprising the following steps: (a) microelectrodes, preferably two carbon fibre electrodes or hollow fibre electrodes, are provided, (b) the microelectrodes are connected to a power supply, (c) the electrodes, individually controlled by high-graduation micromanipulators, are placed close to the cell structure at an appropriate inter-electrode distance, and (d) a highly focused electric field of a strength sufficient to obtain electroporation is applied between the electrodes. The method may be used in order to transfer cell impermeant solutes, such as drugs or genes, into the cell structure or out of the cell structure, in biosensors, in the treatment of tumours and neurodegenerative diseases and in the study of biophysical processes.

86 Claims, 7 Drawing Sheets

OTHER PUBLICATIONS

K. Kinosita, Jr., & T. Y. Tsong, T. *Biochim. Biophys. Acta,* 554, 479–497 (1979).

D. C Chang, J. Biophys., 56, 641–652 (1989).

Q. A. Zheng. & D.C. Chang, *Biochim. Biophys. Acta,* 1088, 104–110 (1991).

M. N. Teruel, & T. Meyer *Biophys. J.,* 73, 1785–1796 (1997).

"Characterization of Single–Cell Electroporation by Using Patch–Clamp and Flurescence Microscopy", Ryttsén et al., *Biophysical Journal,* vol. 79 (Oct. 2000) pp. 1993–2001.

"Selective Introduction of Antisense Oligonucleotides into Single Adult CNS Progenitor Cells Using Electroporation Demonstrates the Requirement of STAT3 Activation for CNTF–Induced Gliogenesis", Åberg, et al., *Molecular and Cellular Neuroscience,* vol. 17 (2000) pp. 1–18.

"Electroporation of Single Cells and Tissues with an Electrolyte–filled Capillary", Nokrantz et al., Article submitted to *Analytical Chemistry* pp. 1–25.

"Electroporation of cell membranes," Tsong, T. Y., *J. Biophysical Society, vol. 60,* 1991 (297–306) (previously filed in 09/557,979 on Aug. 25, 2000).

"Electric field–mediated fusion and related electrical phenomena," Zimmerman, U., *Biochim. Biophys. Acta,* 694, 227–277 (1982) (previously filed in 09/557,979 on Aug. 25, 2000).

"Electroporation: A general phenomenon for manipulating cells and tissues," Weaver, J. C., *J. Cell. Biochem.,* vol. 51, 426–435 (1993) (previously filed in 09/557,979 on Aug. 25, 2000).

"L'électrochimiothérapie, un nouveau traitement antitumoral: prelier essai clinique," Lluis M. Mir et al., C R Acad Sci. III, 1991, 313, 613–618 (article is in French, with Abridged English Version).

"A new brain Tumour therapy combining bleomycin with in vivo electropermeabilization," Leif G. Salford et al., *Biochem. Biophys. Res. Commun.,* 1993, 194, 938–43.

"Electrochemotherapy on liver tumours in rabbits," L. H. Ramirez et al., *Br. J. Cancer,* 1998, 77, 2104–11.

"Efficient gene targeting in mouse embryonic stem cells," N. S. Templeton et al., *Gene Therapy* (1997), vol. 4, pp. 700–709.

"Electrochemotherapy: an emerging drug delivery method for the treatment of cancer," Mark J. Jaroszeski et al., *Advanced Drug Delivery Review,* vol. 26, (1997), pp. 185–197.

"Effects of a high–voltage electrical impulse and an anti-cancer drug on in vivo growing tumors," M. Okino et al., *Jpn J. Cancer Res.,* vol. 78, pp. 1319–1321, Dec. 1987.

\* cited by examiner

METHOD FOR ELECTRO-PERMEABILIZATION OF INDIVIDUAL CELLULAR AND ORGANELLAR STRUCTURES AND USE THEREOF

This is a continuation of International Application No. PCT/SE98/02012, filed Nov. 6, 1998, that designates the United States of America and which claims priority from Swedish Application No. 9704076-0, filed Nov. 6, 1997.

FIELD OF THE INVENTION

The present invention relates to a highly spatially resolved method for permeabilisation of cell structures, organelle structures and cell-like structures in order to transfer compounds into or out of the structures. It also relates to use of this method.

BACKGROUND OF THE INVENTION

During the last two decades there has been a tremendous growth in experimental methods that allow for biochemical and biophysical investigations of single cells. Such methods include patch clamp recordings which can be used for measurement of transmembrane currents through a single ion channel (O. P. Hamill, A. Marty, E. Neher, B. Sakman, F. J. Sigworth, *Pfleugers Arch.* 391, 85–100 (1981)); laser confocal microscopy imaging techniques that can be used to localise bioactive components in single cells and single organelles (S. Maiti, J. B. Shear, R. M. Williams, W. R Zipfel, W. W. Webb, *Science*, 275, 530–532 (1997)); use of near field optical probes for pH measurements in the cell interior; and use of ultramicroelectrodes for measurement of release of single catechol- and indol-amine-containing vesicles (R. H. Chow, L. von Ruden, E. Neher, *Nature*, 356, 60–63 (1992) and R. M. Wightman, J. A. Jankowski, R. T. Kennedy, K. T. Kawagoe, T. J. Scroeder, D. J. Leszczyszyn, J. A. Near, E. J. Diliberto Jr., O. H. Viveros, *Proc. Natl. Acad. Sci. U.S.A.*, 88, 10754–10758 (1991)). Although numerous high-resolution techniques exist to detect, image and analyse the contents of single cells and subcellular organelles, few methods exist to control and manipulate the biochemical nature of these compartments. Most compounds for biological and medical use that are of interest to include in cells are polar. Polar solutes are cell-impermeant and unable to pass biological membranes unless specific transporters exist. Often in experimental biology as well as in biochemical and clinical work, polar solutes need to be administered to the cytoplasm of cells or to the interior of organelles. Examples of such polar solutes are nanoparticles, dyes, drugs, DNAs, RNAs, proteins, peptides, and amino acids. At present, it is extremely difficult, for example, to label a cell in a cell culture with a dye, or transfect it with a gene without labelling or transfecting its adjacent neighbour. It is even more difficult to introduce polar molecules into organelles because of their size which many times is smaller than the resolution limit of a light microscope, or at least less than a few micrometers in diameter.

Microinjection techniques for single cells and single nuclei have also been described (see e.g. M. R. Capecchi, *Cell*, 22, 479–488 (1980), but these get increasingly difficult to implement as the size of the cell or organelle decreases. For cells and organelles measuring only a few micrometers in diameter or less, microinjection techniques become virtually impossible to use.

It has for a long time been recognised that cell membranes can be permeabilised by pulsed electric fields (see e.g. Zimmermann, U. *Biochim. Biophys Acta*, 694, 227–277 (1982); Tsong, T. Y. *Biophys. J.*, 60, 297–306 (1991); Weaver, J. C. *J. Cell. Biochem.*, 51, 426–435 (1993)). This technique is called electroporation. The membrane voltage, $V_m$, at different loci on phospholipid bilayer spheres during exposure in a homogenous electric field of duration t, can be calculated from:

$$V_m = 1.5 r_c E \cos\alpha [1-\exp(-\tau/t)] \qquad (1)$$

where E is the electric field strength, $r_c$ is the cell radius, $\alpha$, the angle in relation to the direction of the electric field, and $\tau$ the capacitive-resistive time constant. Pore-formation will result at spherical coordinates exposed to a maximal potential shift, which is at the poles facing the electrodes ($\cos\alpha=1$ for $\alpha=0$; $\cos\alpha=-1$ for $\alpha=\pi$). Generally, electric field strengths on the order of from 1 to 1.5 kV/cm for durations of a few $\mu$s to a few ms are sufficient to cause transient permeabilisation in 10-$\mu$m-outer diameter spherical cells. A recent study shows that isolated mitochondria, because of their correspondingly smaller size, require 7–10-fold higher electric field strengths to incorporate a 7.2-kilobase plasmid DNA (J-M. Collombet, V. C. Wheeler, F. Vogel, & C. Coutelle *J. Biol. Chem.*, 272, 5342–5347 (1997)). Mitochondrial outer-membrane fusion at lower electric field strengths of about 2.5 kV/cm has also been observed.

Traditionally, electroporation is made in a batch mode allowing for administration of polar solutes into several millions of cells simultaneously. The electrodes producing such fields can be several square centimetres and the distance between the electrodes several centimetres, thus requiring high-voltage power sources to obtain the needed electrical field strength to cause electrically induced permeabilisation of biological membranes.

One advantage of electroporation compared to microinjection techniques is that electroporation can be extremely fast, and precisely timed (see e.g. K. Kinosita, K., Jr., I. Ashikawa, N. Saita, H. Yoshimura, H. Itoh, K. Nagayama, & A. Ikegami *J. Biophys.*, 53, 1015–1019 (1988); M. Hibino, M. Shigemori, H. Itoh, K. Nagayama, & K. Kinosita, K., Jr., *Biophys. J.*, 59, 209–220 (1991)) which is of importance in studying fast reaction phenomena.

Instrumentation that can be used for electroporation of a small number of cells in suspension (K. Kinosita, Jr., & T. Y. Tsong, T. *Biochim. Biophys. Acta*, 554, 479–497 (1979); D. C Chang, *J. Biophys.*, 56, 641–652 (1989; P. E. Marszalek, B. Farrel, P. Verdugo, & J. M. Fernandez, *Biophys. J.*, 73, 1160–1168 (1997)) and for a small number of adherent cells grown on a substratum (Q. A. Zheng, & D. C. Chang, *Biochim. Biophys. Acta*, 1088, 104–110 (1991); M. N. Teruel, & T. Meyer *Biophys. J.*, 73, 1785–1796 (1997)) have also been described. The design of the electroporation device constructed by Marszalek et al. is based on 6 mm long 80 $\mu$m diameter platinum wires that are glued in a parallel arrangement at a fixed distance of 100 $\mu$m to a single glass micropipette. The design by Kinosita and Tsong uses fixed brass electrodes spaced with a gap distance of 2 mm, the microporator design of Teruel and Meyer relies on two platinum electrodes that are spaced with a gap distance of about 5 mm, and the electroporation chamber design by Chang uses approximately 1 mm-long platinum wires spaced at a distance of 0.4 mm. It is obvious, that these electroporation devices, which are optimized for usage in vitro, create electric fields that are several orders of magnitude larger than the size of a single cell which typically is 10 $\mu$m in diameter, and thus can not be used for exclusive electroporation of a single cell or a single organelle or for electroporation inside a single cell. The techniques do not offer a sufficient positional and individual control of the electrodes to select a single cell, or a small population of cells. Furthermore, these techniques are not optimized for electroporation in vivo or for electroporation of remote cells and tissue. Electroporation devices for clinical and in vivo applications have also been designed. Examples include devices for electroporation-mediated delivery of drugs and genes to tumours (WO 96/39226) and to blood cells (U.S. Pat. No. 5,501,662) and to remote cells and tissue (U.S. Pat. No. 5,389,069). Likewise, these can not be used to create a highly localised electric field for electroporation of a single cell, a single organelle, or a population of organelles within a cell.

SUMMARY OF THE INVENTION

One of the major disadvantages with the known techniques is that they are not applicable for permeabilisation of single cells or single intracellular organelles.

The present invention provides a highly spatially resolved technique to alter the biochemical content of single cells and organelles, based on permeabilisation of phospholipid bilayer membranes by pulsed electric fields, i.e. so called electroporation.

An advantage the method according to the present invention compared to known methods for electroporation is that the method according to the invention is characterised by an extremely high spatial resolution defined by highly focused permeabilising electric fields. Such highly focused electric fields are obtained by using a pair of electroporation electrodes with outer diameters in the range of a few manometres to a few micrometers. This enables electroporation of single cells and even intracellular structures. The electrodes are controlled individually with high-graduation micropositioners, thereby enabling precise electrode alignment with respect to a structure to be permeabilised. During the effective pore-open time, cell-impermeant solutes added to the extracellular or extraorganellar medium can enter the cell or organelle interior by diffusion.

In contrast to the known microinjection techniques for single-cells and single nuclei, the present invention can be applied for biological containers of subfemtoliter ($<10^{-15}$ l) volumes or less than a few micrometers in diameter, which is another important advantage of the invention.

Furthermore, the present invention distinguishes itself from prior art in that electroporation with single-cell or subcellular spatial resolution is accomplished by applying the electric field through nanometer- and micrometer-diameter electrodes with extremely short inter-electrode distances. The electrodes are controlled individually by high-graduation micromanipulators, allowing precise focusing of the electric field between the electrodes. Electroporation of individual cells and individual organelles can thereby be accomplished. Electroporation can with the present invention be performed in such a way that only a target cell is permeabilised and not its adjacent neighbour. Also, individual cellular processes can be electroporated. Even spatially well-defined intracellular domains with a targeted class of organelles can be held under a localised electric field with this invention, thereby enabling transfer of polar solutes into organelles. Applications of electroporation of organelles include alterations of the mitochondrial genome. It is well known that mutations in the mitochondrial genome can lead to a multitude of diseases, and that gene therapy can potentially be of major importance. So far, however, mitochondria has to be isolated from the cells before transfer of the new genefragment into the mitochondria can be performed. Then, the mitochondria has to be reinserted into the cell. The technique according to the invention makes it possible to directly insert genes into the mitochondria when they are contained inside a cell. This is a significant advancement over traditional schemes for transfection of mitochondria.

In addition to the high spatial resolution achieved by using nano- and micro-electrodes, the technique according to the invention avoids the use of expensive high-voltage pulse generators, and complicated microchamber mounts. The method according to the invention can in principle be battery-operated because the spacing between the electrodes is small, typically 20 $\mu$m or less, which result in a high electric field strength with a small amplitude voltage pulse. This technique is the first demonstration of selective solute-transfer into biological structures using highly focused electric fields of single-cell and subcellular dimensions.

The method according to the invention can be additionally used for biosensor applications where a cell or a cell-like structure is placed in a permebilising dc or ac electric field while supplemented with drugs or other compounds of interest. A special application is the combination of electroporation and miniaturised chemical separations, where hollow liquid electrodes made of fused silica or similar materials are used.

With ultramicroelectrodes, such as carbon fibre electrodes, controlled by high-graduation micromanipulators, used according to the present invention, it is easy to focus the electrical field to very well-defined regions.

Thus, the present invention relates to a method for permeabilisation of a cell structure consisting of a small population of cells, a single cell, an intracellular structure or an organelle, characterised in that it enables highly spatially resolved permeabilisation and that it comprises the following steps:

(a) at least one microelectrode is provided;
(b) said at least one microelectrode is connected to a power supply;
(c) said at least one microelectrode, individually controlled by high-graduation micromanipulators, is placed close to the cell structure;
(d) a highly focused electric field of a strength sufficient to obtain electroporation is applied between said at least one microelectrode and at least one other electrode also connected to said power supply.

One embodiment of the invention relates to a method for permeabilisation of a cell structure consisting of a single cell or a cell-like structure, an intracellular structure or an organelle characterised in that it comprises the following steps:

(a) microelectrodes are provided;
(b) the microelectrodes are connected to a power supply;
(c) the electrodes, individually controlled by high-graduation micromanipulators, are placed close to the cell or organelle structure or inside a single cell at an appropriate inter-electrode distance using high-graduation micromanipulators;
(e) a highly focused electric field of a strength sufficient to obtain electroporation is applied between the electrodes.

The cell structure can be any kind of cell or cell-like structure, such as a cell in a primary cell culture, a cell in a tissue slice or a tissue, an in vivo cell, a liposome, or an intracellular cell structure, such as an organelle,.

The method according to the invention may be used either for transferring solutes from an extracellular medium into a permeabilised cell structure, or for transferring solutes entrapped in the cell structure out to the extracellular medium. The method according to the invention may also be used for transferring a substance into or out from an organelle, even when the organelle is located inside a cell.

The method is well-suited for the study of cellular migration, proliferation, growth, and differentiation, as well as a multitude of biochemical and biophysical events. It also opens up new possibilities for highly spatially resolved distribution of nanoparticles, drugs, genes and different biochemical markers, such as dyes into single cells or organelles both isolated and in situ. The method may be useful in clinical applications as a vehicle to administer drugs and genes to patients.

The method may also be useful for biosensor applications. In particular, a single cell can be placed in a permeabilising ac or dc field, thereby allowing cell-impermeant molecules that affect intracellular chemistry, including activation of receptors present on the surface of various organelles to be activated. In this way a compound library that acts on intracellular chemistry can be screened for biological activity. The compounds of interest can then be added to the cell solution using a perfusion system or a syringe. In a special case the compounds of interest can be delivered by a fused silica electrophoresis capillary of narrow inner dimensions. Because the electrophoresis capillary is connected to a voltage source, the electrophoresis capillary can be viewed as a liquid-filled electrode. If the outlet end of the electrophoresis capillary is placed close enough to the cell membrane, and an electric field strength sufficient to cause dielectric membrane breakdown is applied, compounds injected into the capillary will cross the cell-membrane barrier and enter the cell interior where they can act on intracellular receptors and intracellular chemistry. Because electrophoresis is a chemical separation technique, it can be used as a fractionation and screening method for biologically important compounds.

The characterising features of the invention will be evident from the following description and the appended claims.

BRIEF DESCRIPTION OF THE DRAWINGS

In the description and the examples below reference is made to the accompanying drawings on which:

FIG. 2A illustrates the situation before electroporation, when all solutes are present in the extracellular volume. FIG. 2B illustrates the situation during application of a voltage pulse when a highly focused electrical field is created over the cell resulting in permeabilisation and diffusion of the solutes into the cell. FIG. 2C illustrates the situation after the electroporation when the membrane pores are resealed and the solutes are trapped inside the cell. It is also feasible at high electric field strengths to electroporate intracellular organelles using this scheme. This results in pore-formation both in the cell membrane and in the organellar structures.

FIG. 3A shows a pair of electrodes inserted into a cell. The electrode tips are placed so that an organelle to be permeabilised is located between the electrode tips. FIG. 3B shows application of an electric field of a strength sufficient to cause pore-formation in the organelles. Organelle-impermeant molecules injected to the cell can thereby diffuse into the organelle. In FIG. 3C the electrodes are withdrawn, excess molecules are removed from the cytoplasm, and the molecules are exclusively located inside a population of permeabilised organelles.

FIG. 4A shows a liquid-filled fused silica electrode with its outlet placed close to the membrane of a single cell. The electrolyte inside the capillary electrode contains cell-impermeant molecules. FIG. 4A illustrates the situation when a permebilising field is applied and the molecules contained in the electrolyte migrate by electroosmosis and electrophoresis, to the outlet end of the capillary electrode.

FIG. 6A is a brightfield image of two progenitor cells. The cell on the top was electroporated in the presence of fluorescein.

FIG. 7A shows two cells electroporated at plasma membrane superthreshold potentials of approximately 2 V (ten pulses at 0.5 Hz repetition rate), both of which display a punctuate cytoplasmic fluorescence pattern due to incorporation of dye into organelles. FIG. 7B shows images of three cells after electroporation at the plasma membrane threshold potential of about 1 V (ten pulses at 0.5 Hz repetition rate) where the fluorescence is diffuse and evenly distributed over the entire cell, demonstrating electroporation of fluorescein into the cytoplasm of the cells.

DETAILED DESCRIPTION OF THE INVENTION

Figure 1:
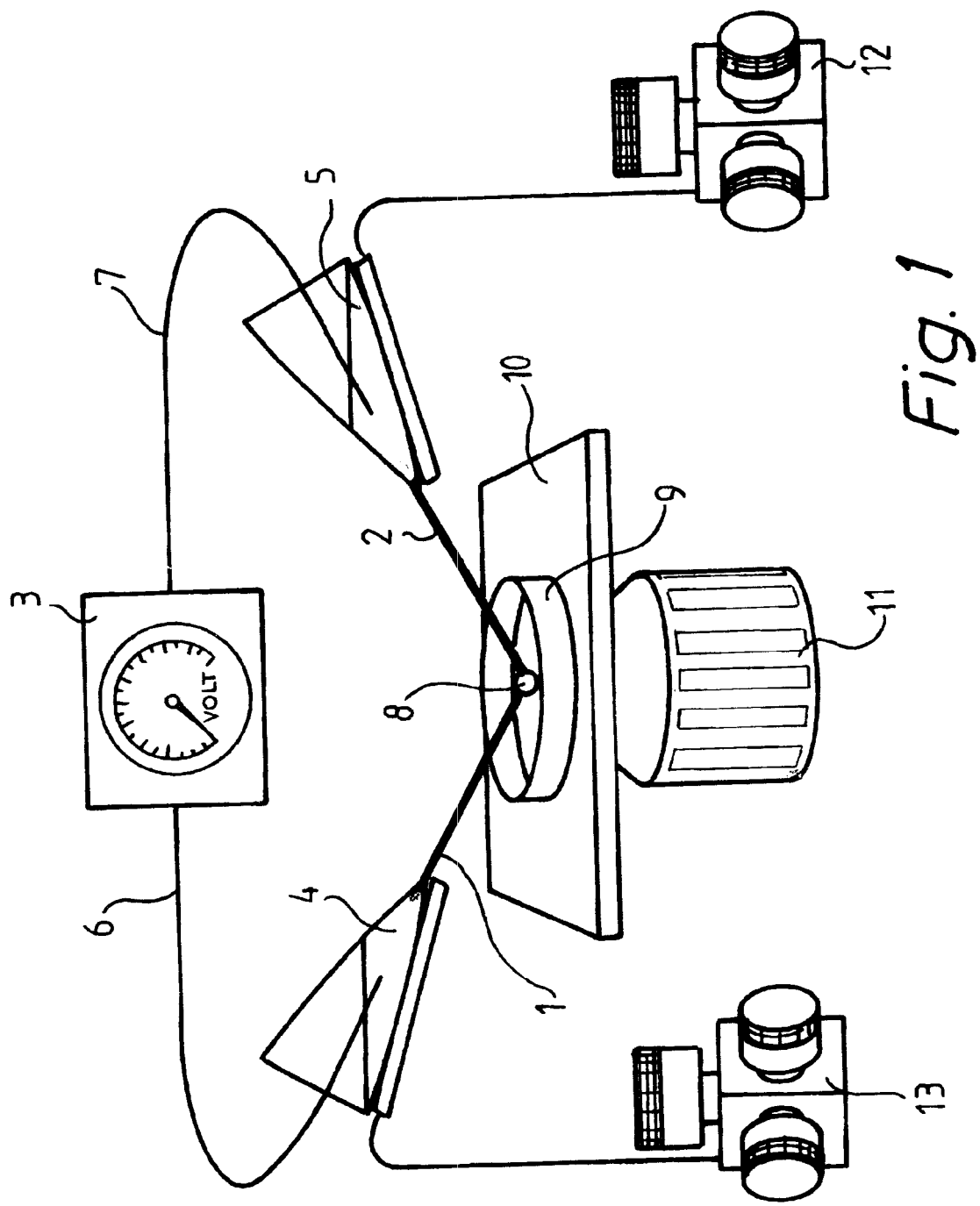
FIG. 1 shows a preferred embodiment of an apparatus used for carrying out the method according to the invention.

With the method according to the present invention it is possible to permeabilise cell structures or cell-like structures and thereby to transfer polar, cell-impermeant solutes, such as nanoparticles, drugs, dyes, RNA, DNA, proteins, and peptides, into or out of cell-like structures. The technique is based on the use of a highly focused electric field that is applied over the cell structure by means of microelectrodes placed close to the cell structure and a voltage source. The microelectrodes are controlled by micromanipulators, preferably high-graduation micromanipulators, and can be translated in three-dimensional space in increments of tens to a few hundreds of nanometres. Preferably two microelectrodes are used, these can be made of carbon fibre, metal or other electrically conductive material. The electrodes can be hollow for administration of, for example, drugs, genes, or dyes through the inner channel. The electrical current needed for electroporation of a cell structure can also be carried by an electrolyte contained in the inner channel.

Such hollow capillary electrodes can be made of fused silica or similar materials, thereby enabling delivery of the drug, gene, or dye to the cell or organelle through electrophoresis or electroosmosis. The diameter of the electrodes are preferably only a few nanometres to a few micrometers in diameter. In the case of hollow electrodes, the inner channel diameter can be a few nanometres to a few tens of micrometers in diameter, whereas the outer diameter can be a few micrometers to several hundred micrometers. Preferably, two microelectrodes are used. However, a single microelectrode for electroporation can be used together with a mesoscopic or larger electrode held at ground or at negative potential. The electrodes can be placed adjacent to a cell for electroporation of the cell membrane and organelles contained inside the cell or the electrodes can be placed inside the cell for exclusive electroporation of the organelles contained inside the cell.

The voltage source generates a voltage pulse, with a waveform that can be square, exponential, or of any other form. It is also possible to use both DC currents and AC currents.

The electrical fields needed to cause electroporation varies largely depending on the type and the size of the treated cell structure. The appropriate field strength can be calculated by man skilled in the art by using see equation 1 given in the background description of this application. The electric field strength is adjusted by the voltage and the inter-electrode distance. Appropriate field strengths may be in the range of from 0.01 kV/cm to 100 kV/cm. Appropriate inter-electrode distances are distances smaller than 10 mm, preferably smaller than 100 μm. If a single mammalian cell is to be treated it may be appropriate to use an inter-electrode distance of from 0.1 μm to 30 μm, and a voltage of from 100 mV to 100 V.

The duration of the voltage pulse may vary from a few microseconds to several minutes, also depending on the type and the size of the treated cell structure. The length of the voltage pulse is preferably from 1 μs to 500 ms.

During application of the voltage pulse, the cell structure is permeabilised through pore formation, allowing polar solutes which otherwise can not pass biological bilayer membranes, to enter or escape the interior of the cell structure through diffusion. The spatial resolution of the method according to the invention is dictated by the size of the electrodes, which can be made to be only a few nanometres in diameter, and the gap distance between the electrodes, which can be made to be a few nanometres to a few micrometers, thereby allowing for electroporation even of the smallest of intracellular organelles and e.g. nanobacteria.

When the method according to the invention is used for transferring biological markers, nanoparticles, dyes, and other particles into cell structures some of the applications are the study of cellular migration, proliferation, growth, differentiation, as well as other biochemical and biophysical events. The method might prove useful in clinical applications as a vehicle to administer drugs and genes to patients. For clinical applications, in particular, a hollow electrode configuration is suitable in which the compound to be electroporated into the cell is administered through a small channel in the electrode.

When the method according to the invention is performed in vitro in order to transfer solutes into a cell structure, such as a tissue slice, a primary culture, a cell line or a preparation of an organelle, an appropriate apparatus may be the preferred embodiment illustrated in FIG. 1, comprising two carbon fibre microelectrodes 1, 2, with outer diameters in the nanometre-to-micrometer size range, connected to a voltage generator 3. Preferably, the electrodes are connected to the voltage generator via vials 4, 5, containing for example 3 M KCl, mercury, or silver glue and silver wires 6, 7. The cell structure 8 is typically held in e.g. a petri dish 9 in some kind of physiological buffer supplemented with the compound to be incorporated into the cell. In order to facilitate viewing and hence positioning of the electrodes in relation to the cell structure it is possible to use a microscope. In the preferred embodiment shown in FIG. 1 the petri dish is situated on an inverted microscope stage 10, and viewed through a microscope objective 11. The electrodes 1, 2, are, by means of three-dimensional micropositioners 12, 13, preferably of a high graduation type, positioned close to each side of the cell structure, preferably in an opposing linear arrangement so that the electrodes face each other with the cell structure in the middle. This is performed in such a way that the electric field produced between the electrodes is highly focused over the structure to be electroporated.

Since the distance between the tips of the electrodes is very short, just a few micrometers, only a low-voltage generator is typically needed to produce the required electrical field strengths for electroporation of biological membranes. Preferably, a rectangular DC voltage pulse is applied over the cell and pores are created in the membrane through which solutes diffuse into the interior down their concentration gradient.

Depending on the composition of the buffer the conditions are changed at the electrodes. Electrochemical reactions at the electrodes, e.g. reduction of water and oxidation of chloride, causes some loss in voltage and the effective voltage should be calculated for every given set of electrode materials and buffer systems.

Figure 2:
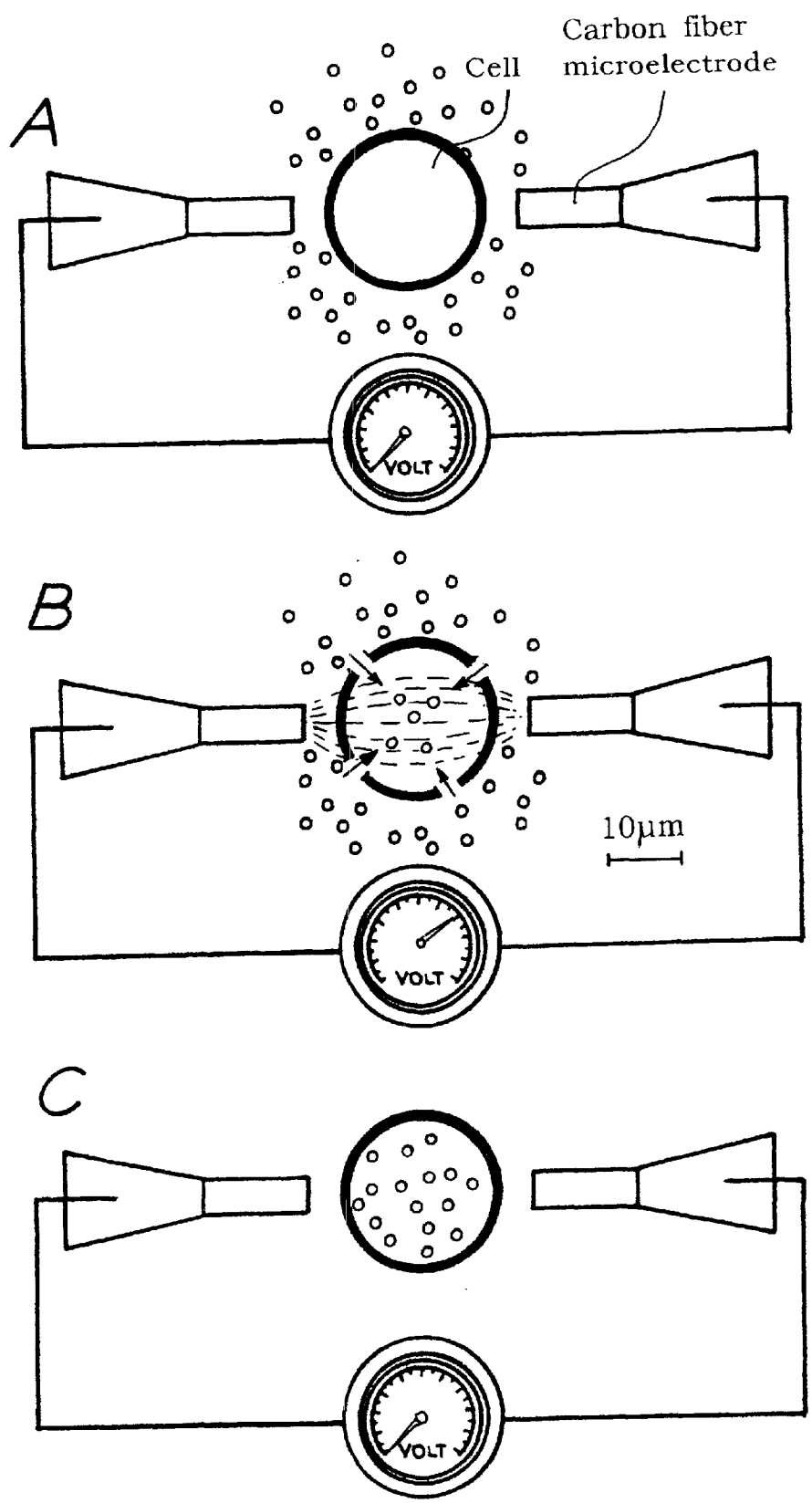
FIGS. 2A–C are schematic drawings of the positioning of the electrodes and the electrical field for electroporation of a single cell.

FIGS. 2A–C are schematic drawings of the positioning of the electrodes and the electrical field for electroporation of a single cell. FIG. 2A illustrates the situation before electroporation, when all solutes are present in the extracellular volume. FIG. 2B illustrates the situation during application of a voltage pulse when a highly focused electrical field is created over the cell resulting in permeabilisation and diffusion of the solutes into the cell. FIG. 2C illustrates the situation after the electroporation when the membrane pores are resealed and the solutes are trapped inside the cell. It is also feasible at high electric field strengths to electroporate intracellular organelles using this scheme. This result in pore-formation both in the cell membrane and in the organellar structures.

After electroporation of the cell structure, washing of the cell dish can be performed in order to remove excess solutes if needed. The buffer is then replaced by a solute-deficient buffer or a culture media.

With the present invention it is also possible to exclusively electroporate organelles. The organelles can be contained inside a single cell or they can be isolated from a single cell or a population of cells. As stated above, the strengths of the pulse depend on what structure to be electroporated and on the distance between the electrodes. Small organellar structures, like endoplasmic reticuli, and mitochondria, require a higher voltage to create pores in the membrane. The pulse duration can also be varied in the range of a few microseconds to several minutes depending on membrane structure but also on the structure of the compound to be incorporated. Large molecules with low diffusion rates require longer periods of time to move into the cell. For electroporation of organelles inside a cell, intracellular electroporation electrodes are preferentially used. These electrodes can have electrically insulating shanks, so that the part of the electrode that comes into contact with the cell membrane does not result in electrically-induced pore-formation. The tips of the electrodes can be made of electrically conductive materials, such as deposited metals, or carbon fibre. Alternatively, hollow-fibre electrodes filled with an electrolyte can be used for such purposes. The physical dimensions of intracellular electrodes for electroporation of organelles can range from a few nanometres to a few micrometers in diameter.

Figure 3:
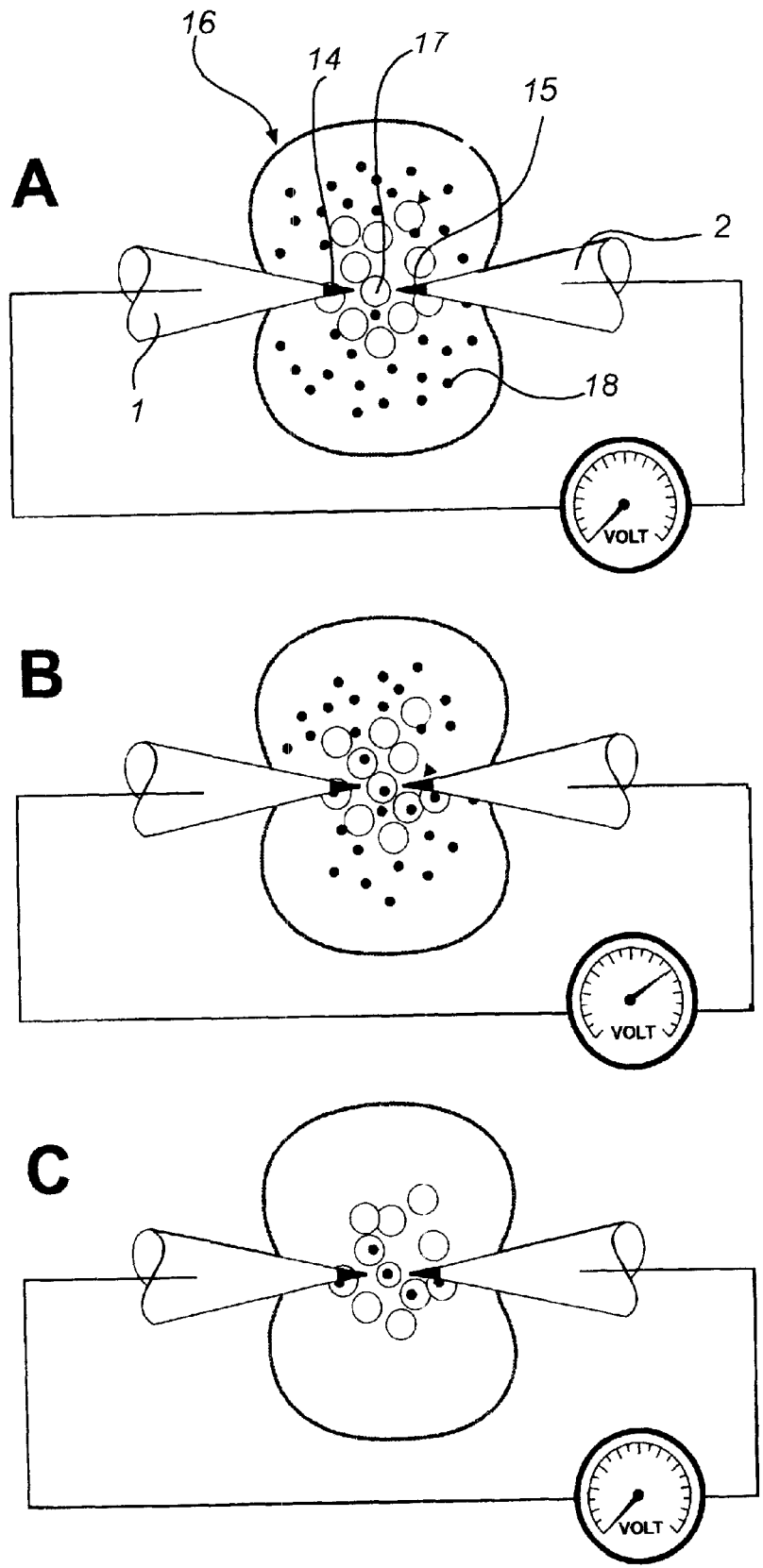
FIG. 3 shows a set-up that can be used for electroporation of intracellular organelles

A preferred embodiment for electroporation of intracellular organelles is shown in FIG. 3. The electrodes 1, 2 used in this set-up have a sharp tip 14, 15 that is made of a conductive material, and electrically insulated shanks. The tip diameter of such electrodes is between a few nanometres and a few micrometers in diameter. FIG. 3A shows a pair of electrodes 1, 2 inserted into a cell surrounded by a cell membrane 16. The insertion and positioning of the electrodes is performed with high-graduation micromanipulators (not shown). The electrode tips 14, 15 are placed at an intracellular domain of interest. The electrodes are arranged so that the organelle 17 to be permeabilised is located between the electrode tips. In FIG. 3B an electric field of a strength sufficient to cause pore-formation in the organelle 17 has been applied. Organelle-impermeant molecules 18 injected to the cell with a microsyringe, or by some other means, can thereby diffuse into the permeabilised organelle 17. This procedure is repeated until the desired number of organelles have been permeabilised In FIG. 3C the electrodes are withdrawn, excess molecules are removed from the cytoplasm using degradative pathways, or by some other means, and the molecules are exclusively located inside a population of permeabilised organelles.

Another application of the present invention is for use with biosensor techniques. In particular, by applying a permeabilising electric field over a single cell, intracellular chemistry and organelles can be used for biosensing purposes. As an example, inositoltriphosphate, which activates receptors on endoplasmic reticuli, can be assayed for using such schemes. The compound is simply added to the buffer surrounding the permeabilised cell and will diffuse into the cell interior and bind to receptors on endoplasmic reticuli. Upon binding of inositoltriphosphate to the receptors, endoplasmic reticuli will liberate calcium ions. If the cell is then supplemented with a fluorogenic calcium chelating dye, such as fluo-3, the receptor activation can be measured as an increase in fluorescence.

Figure 4:
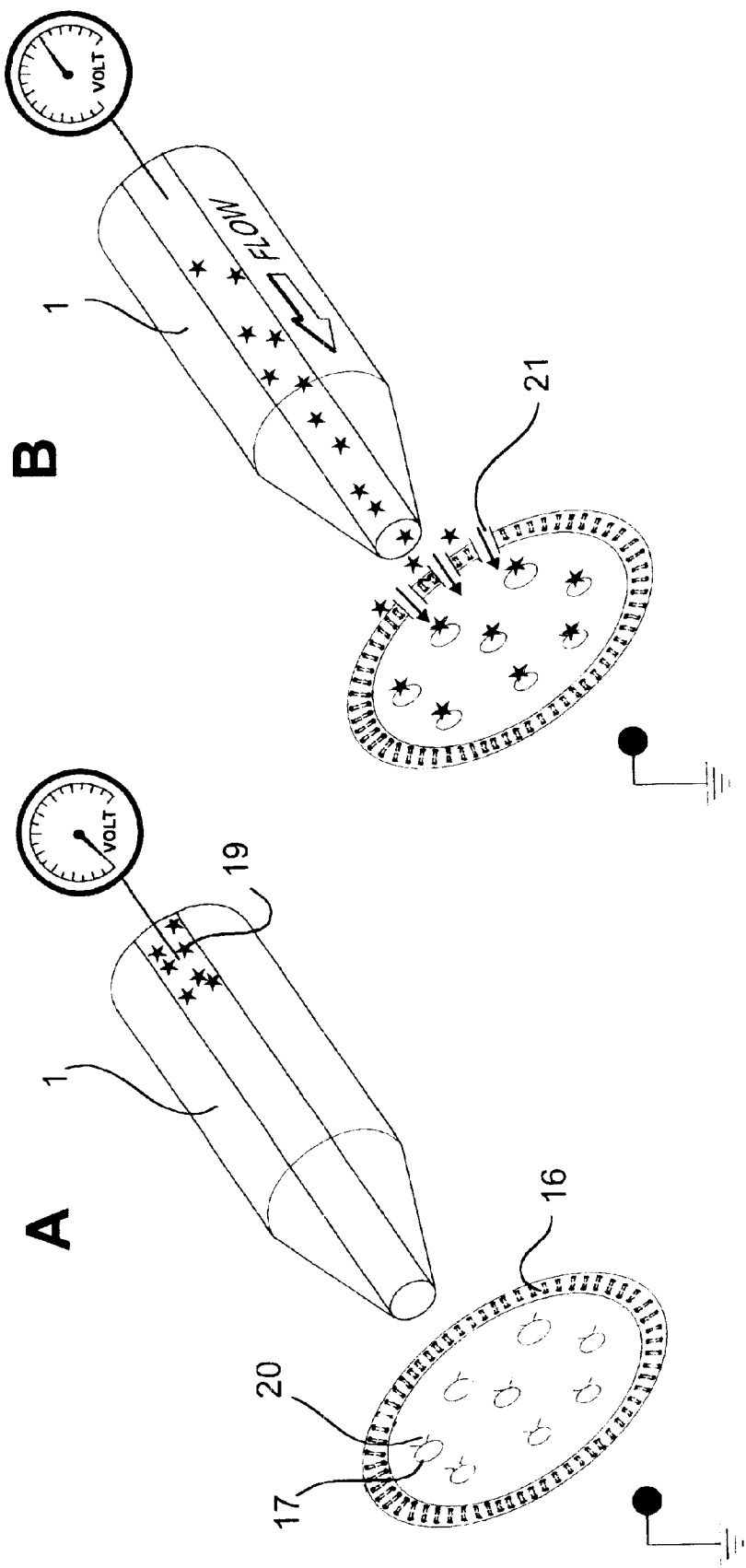
FIGS. 4A and B show electroporation of cells using electrolyte-filled electrodes.

When hollow fibre electrodes are used, according to the present invention, the cell-impermeant molecules added to the intra-electrode solution can be administered to the cell using a perfusion system, such as a microsyringe pump or a peristaltic pump. According to another scheme, electrolyte-filled fused silica capillaries with narrow inner diameters are used as electroporation electrodes. With these electrodes, the cell-impermeant molecules contained in the electrolyte solution can be delivered to a cell using electrophoresis or electroosmosis as shown in FIG. 4. The applied electric field causes pore formation in the cell as previously discussed. Because the components inside the electrode electrolyte will be separated based on their charge-to-frictional drag ratio, this method can be used for, for example, biosensor applications. For electroporation of cells it is possible to use either electrodes with conductive tip for application of the electric field necessary to create pore-formation or electrodes filled with an electrolyte that carries the electric current necessary to create pore-formation. In the case of electrodes with an conductive tip, cell-impermeant molecules supplemented to the liquid contained in the hollow electrodes can be administered to the cell using a perfusion system, such as a syringe pump or peristaltic pump. In the case of using hollow electrodes in which the permeabilising current is carried by the electrolyte, the molecules contained in the electrolyte of the hollow electrode can additionally be delivered to the cell structure by electrophoresis or electroosmosis. When using electrophoresis or electroosmosis, the components in the hollow electrode can be separated based on their charge-to-frictional-drag ratio. This opens up possibilities for performing organelle-sensor-based detection of species fractionated by electrophoresis.

Electroporation of cells using liquid-filled fused silica electrodes with tapered tips is illustrated in FIGS. 4A and B. Such tapered tips can be created by pulling the fused silica capillary in a flame, etching in hydrofluoric acid, or by grinding.

FIG. 4A shows an electrolyte-filled fused silica electrode 1 with its tapered outlet placed close to the membrane 16 of a single cell. The electrolyte inside the capillary contains cell-impermeant molecules 19 injected into the capillary hydrodynamically, or by some other means. In this case, the supplemented cell-impermeant molecules 19 activate receptors 20 on organelles 17. When a permebilising field is applied, by application of positive voltage to the inlet end of the capillary electrode, the molecules contained in the electrolyte will migrate by electroosmosis and electrophoresis, to the outlet end of the capillary electrode. Because the electric field is chosen to be strong enough to permeabilise the cell membrane, the cell-impermeant molecules supplemented to the electrolyte contained in the electrode will pass the pores 21 formed in the cell membrane and can, for example, activate receptors on organelles, as shown in FIG. 4B. Because the electric field is chosen to be strong enough to permeabilise the cell membrane, the cell-impermeant molecules supplemented to the electrolyte contained in the electrode will pass the pores formed in the cell membrane and can, for example, activate receptors on organelles. Electrodes of similar sort but of smaller dimension can be used for electroporation of organelles.

If the method according to the invention is carried out in vivo it is possible to use a surgical microscope, in order to view the cell structure. Furthermore, it is possible to use a stereotactic device for the positioning of the electrodes. When the method is performed in vivo it is of course not possible to place the cell structure in some sort of container with buffer. Instead, the compound to be incorporated into the cell structure is administered in a physiological buffer either separately via a catheter or directly via a hollow fibre electrode. When hollow fibre electrodes are used the compound is administered to the cell structure through a small channel in the electrodes which is coupled to a syringe controlled by a micrometer screw or a microinjection pump to enable administration of an exact volume. The possibilities to add the compound either at the same time as he electroporation occurs or with some time delay make this technique very useful. A very high concentration is achieved locally at the selected cell and diffusion into it will be faster due to the greater concentration gradient. The lower consumption of the compound and the minimisation of the problems due to the washing procedure are some other advantages. Many times a focal administration, i.e. administration directly to the malfunctioning set of cells, of drugs or genes can be expected to be far superior than intraperitoneal, oral, intraventricular, or any other kind of commonly employed drug-administration technique. Intracellular drug-and-gene-administration in vivo can be accomplished with the method according to the invention. Because of the extremely small dimensions of the electrodes, in combination with the low voltages applied, very little tissue trauma is expected. Furthermore, the positioning of the electrodes and the subsequent gene or drug delivery is very precise. It has been shown that microdialysis probes, which are on the order of a hundred times larger than the electrodes used in the method according to the present invention, cause very little tissue trauma and disruption of local metabolism.

With the method according to the invention, used in combination with gene therapy, it will be possible to "re-program" cells; either in order to make a malfunctioning cell work in the correct way, or to give a cell a new function.

It is thus possible to use the method according to the invention in therapies for and treatment of different diseases and conditions caused by the malfunction of single cells or a small population of cells, such as Parkinson's disease and brain tumours, which is further illustrated below.

Many diseases, may they be genetically acquired or not, result in metabolic disruptions. For example, Parkinson's disease caused by degeneration of neurons in the Nigrostriatal pathway result in malfunctioning in the biochemical machinery for production of dopamine in an isolated population of cells. This in turn results in motorbehavioral deficits. The standard treatment of Parkinson's disease is by oral administration of L-DOPA, a precursor of dopamine. Alternatively, grafted tissue with neuronal cells producing dopamine is transplanted into the patient's brain. Intracellular drug or gene administration in vivo into the appropriate brain structures can be accomplished using an electroporation procedure similar to that described in the two above examples and used as a therapeutic strategy.

Experimental treatment of brain tumours using genetically engineered viruses for gene delivery has been used with anecdotal reports of success. The use of viruses as a delivery system has limitations in that it might pose a potential hazard if the virus mutate. Using an electroporation procedure for gene delivery, e.g. "suicide genes" for cytokine deaminase or thymidine kinase, similar to that described in the examples below, eliminates the need for the use of virus delivery systems in cancer therapy.

Figure 5:
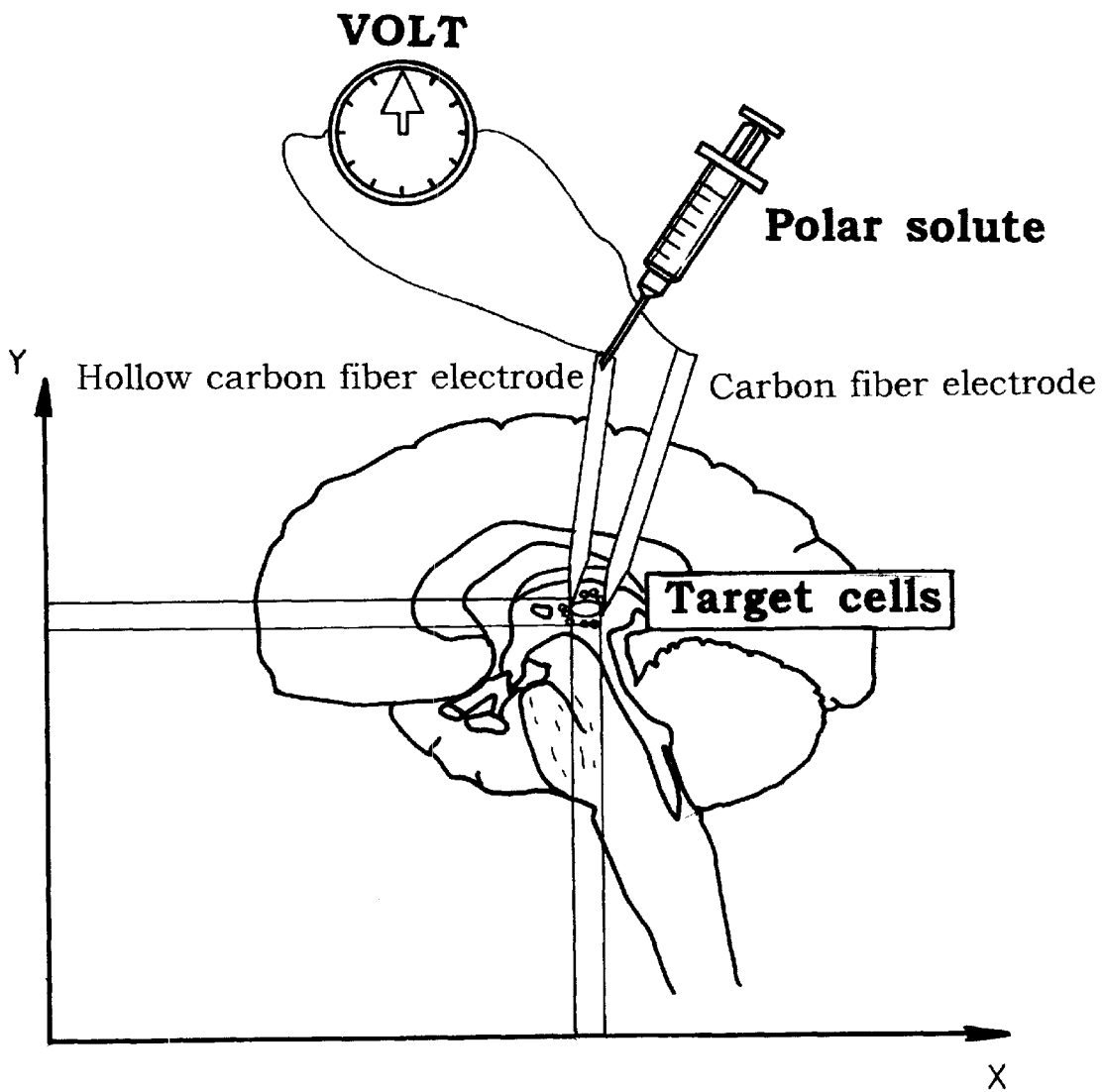
FIG. 5 illustrates an example of a clinical application of the method according to the invention. Two electrodes are placed in a cellular structure in human brain. The positioning of the electrodes can be performed using a stereotactic atlas, represented in the figure by the Cartesian coordinate system, and stereotactic micropositioners. One electrode is hollow for perfusion of e.g. drugs or genes. Perfusion can be achieved as shown here with a syringe or by some other means, including electrophoresis.

FIG. 5 is a schematic illustration of treatment of brain tumours with the method according to the invention. Two electrodes, preferably at least one hollow fibre electrode for perfusion of e.g. drugs or genes, are placed in a cellular structure in human brain. The positioning of the electrodes can be performed using a stereotactic atlas, in the figure represented by the Cartesian co-ordinate system, and stereotactic micropositioners. Perfusion can be achieved as shown in the figure with a syringe or by some other appropriate means. The positioning of the electrodes and the applied electrical field can be varied so a desired number of cells are electroporated.

The solutes to be electroporated into cells are then simply administered through the narrow channel in the centre of the electrode or electrodes by application of a flow by means of a syringe pump or a peristaltic pump or any other type of solution pumping system including electrophoresis.

An especially interesting possibility is to use battery-operated perfusion/electroporation implants in biotolerable materials for continuous application of solutes into cells. Because such low potentials are required, batteries providing voltages in the range of from a few to about 20 volts can be used. These battery-operated electroporation units can be made small, they can be included on a chip measuring only a few millimetres squared. Such a system could include a solute-containing solution reservoir, two electrodes for electroporation, electronic circuitry for timed delivery and control of the electroporation parameters, i.e. pulse profile, pulse duration, repeat, and amplitude as well as a battery source, and a reservoir refill inlet.

The electrodes used according to the present invention may have any appropriate shape or configuration. They may be of the type illustrated in FIG. 1. They may also, for example, be one pair or several pairs of rod-like electrodes that penetrate the full length of the structure to be electroporated. When an electric field is applied over these rod-like electrodes all cells exposed will be electroporated. This allows for a higher turn over number and faster treatments.

When the method according to the invention is used for transferring entrapped solutes out of cell structures, so called reversed electroporation, some of the applications are drug delivery to single cells or small populations of cells. This is e.g. used in order to permeabilise cells and cell-like structures, such as liposomes in order to transfer cell impermeant solutes from their inside to the extracellular media. The concentration gradient for the solutes then have the opposite direction i.e. high solute concentrations inside the cell structure and low solute concentrations outside the cell structure. In particular, liposomes with entrapped drugs can be emptied in a controlled way close to a target cell simply by applying a DC voltage pulse over its membrane through carbon fibre microelectrodes positioned in the same way as described above. The use of such liposome-based delivery of drugs triggered by electroporation can be used in basic research as well as in the pharmaceutical industry, e.g. for compositions with delayed release.

It is also possible to make cells discharge solutes present in their cytoplasm by application of an electric field identical as described above for solute-transfer into cells using electroporation.

The invention will be further illustrated in the examples below, which in no way limit the scope of the invention.

EXAMPLE 1

Electroporation of Progenitor Cells from Mature Rat Brain to Incorporate a Fluorescent Marker Progenitor cells were cultured according to standard procedures (T. D. Palmer, J. Ray, F. H. Gage, *Mol. Cell. Neurosci.*, 6, 474–486 (1995)) and plated onto number 1, 1-inch circular coverslips coated with poly-D-ornithine and lamilin. The cells were allowed to stand overnight to adhere to the glass surface. The cells were incubated in a humid atmosphere at 37° C. with 5% $CO_2$ and 95% air. For the electroporation, the cell dishes were mounted into a circular low-rim polycarbonate holder using mounting grease. The polycarbonate holder with the cover slip was mounted on the stage of an inverted microscope (Leica DM IRB). The cells were held in a HEPES-buffered saline containing 137 mM NaCl, 0.4 mM $MgCl_2$, 0.64 mM $KH_2PO_4$, 3.0 mM $NaHCO_3$, 0.41 mM $MgSO_4$, 5.4 mM KCl, 20 mM HEPES, 1.26 mM $CaCl_2$, and 5.5 mM D-glucose (pH adjusted to 7.4 with NaOH). This HEPES buffer was supplemented with fluorescein (sodium salt, 5 $\mu$M), a highly fluorescent charged species.

To electroporate the cells, two carbon fibre microelectrodes (Pro CFE, Axon Instruments, Foster City, Calif.) connected with the power supply by a liquid junction of KCl (3 M) and a thin silver wire, were placed in the cell bath with a distance of about 15 $\mu$m between the tips and with the cell positioned in the centre between the two tips. This configuration is illustrated in FIG. 3A. Electroporation of the cell membrane was accomplished by applying one-to-ten pulses of DC voltage yielding membrane potentials of 0.5-to-1 V with a duration of about 1 ms over the tips using a low-voltage pulse generator (Digitimer Stimulator, DS9A, UK). It should be noted that different voltages, durations, pulse profiles, and also alternating currents can be employed if needed. During application of the voltage pulse, a highly focused electrical field is created over the cell. The presence of the field results in permeabilisation of the cell through pore formation and the solute molecules diffuses into the cell down their concentration gradient, which is illustrated in FIG. 3B. Following application of the electrical pulse the membrane pores are resealed and the analytes are then trapped inside the cell. Finally, the cell dishes were washed with HEPES buffer solution. The final situation is illustrated in FIG. 3C.

Figure 6:
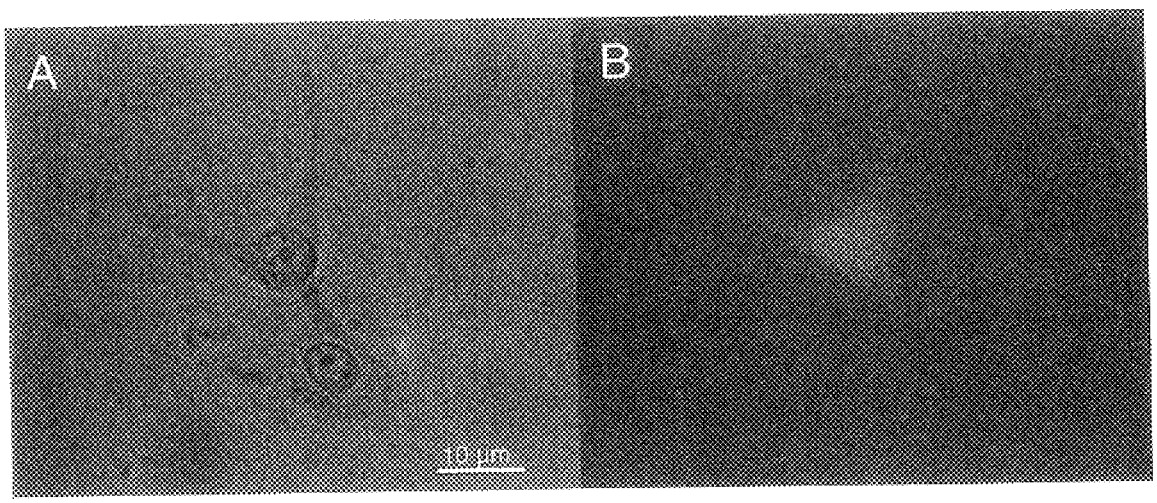
FIGS. 6A and B show video images taken through a microscope demonstrating electroporation of progenitor cells to incorporate fluorescein.
FIG. 6B is a fluorescence image demonstrating that the fluorescence is uniquely localised to the upper cell with virtually zero spillover of fluorescein to the neighbouring cell.

The cells were then viewed in the microscope using excitation of the fluorescein at 488 nm using an Ar-ion laser (Spectra Physics model 2025-05, Sunnyvale, Calif.). The laser light was sent through a 488-line interference filter followed by a spinning disk to break the coherence and scatter the laser light. The laser was collected by a lens and sent through a fluorescein filter cube (Leica I-3) into the objective to excite the fluorphores. The resulting fluorescence was collected by the same objective and the image was detected by a 3-chip colour CCD-camera (Panasonic) and recorded at 25 Hz frame collection rate by a Super VHS (Panasonic SVHS AG-5700). The CCD images were digitised from tape and processed for presentation. The result is shown in FIG. 6. The cell on the top in FIG. 6A, which a brightfield image of two progenitor cells in close contact with each other, was electroporated in the presence of fluorescein as described above. As shown in the fluorescence image in FIG. 6B, the fluorescence is uniquely localised to the upper cell with virtually zero spillover of fluorescein to the neighbouring cell. Thus, with the current electrodes and instrumentation, it is feasible to achieve a sufficient spatial resolution to electroporate single cells.

EXAMPLE 2

Figure 7:
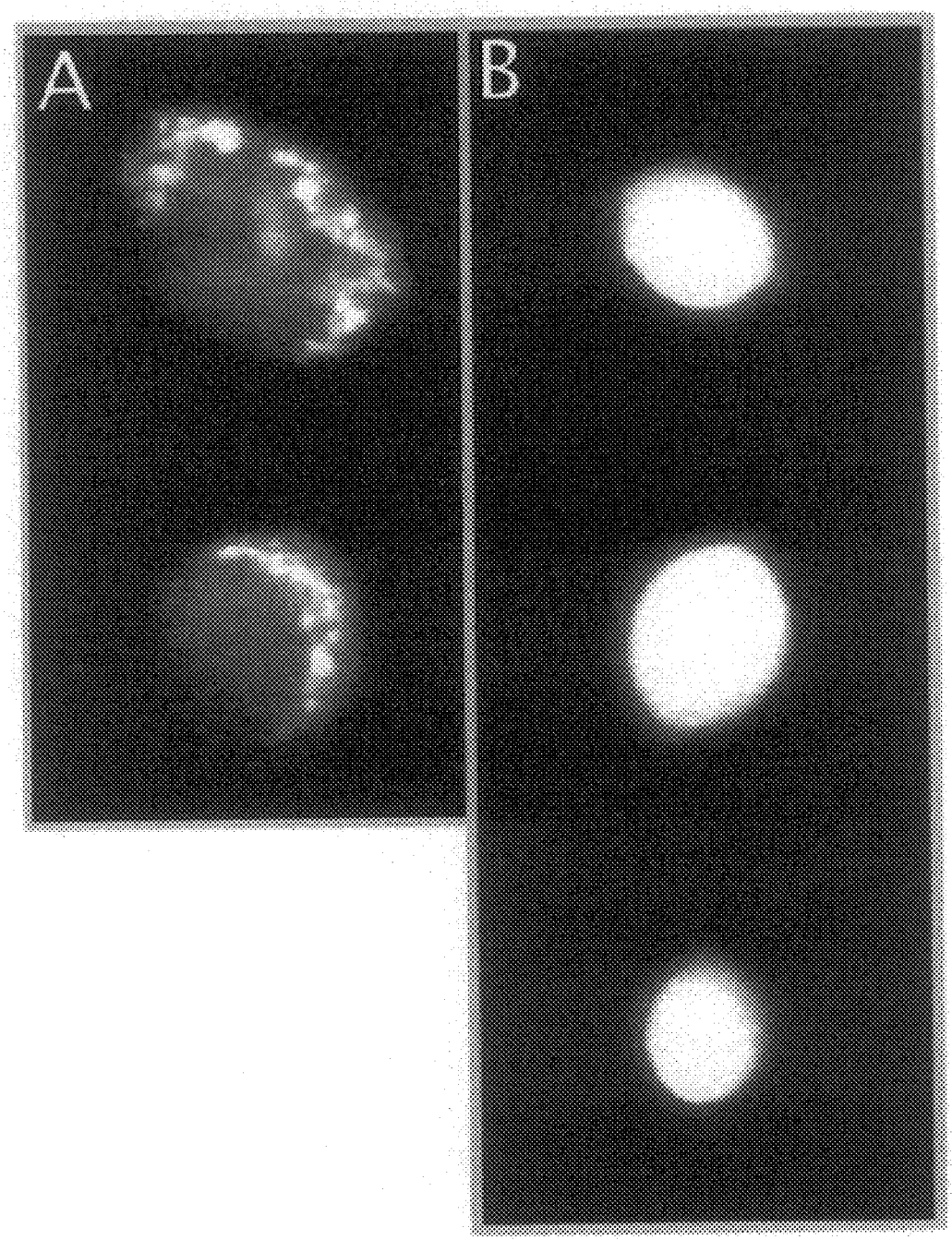
FIG. 7 shows photomicrographs demonstrating differential fluorescence staining resulting from electroporation of fluorescein into single progenitor cells at high, and low electric field strengths, respectively.

Electroporation of Intracellular Organelles in Progenitor Cells from Adult Rat Brain Using Extracellular Electrodes The experimental set-up from example 1 was repeated for in situ electroporation of organelles in single progenitor cells. Specifically, fluorescein was introduced into single cells by ten 0.5-Hz superthreshold field applications resulting in potential shifts at the cell membrane of 1.6 V±0.07 V (range 1.5–2.4 V), and compared to cells electroporated at low membrane potentials of 0.5–1.0 V. Following electroporation, the extracellular dye-containing media was replaced by a Hank Hepes solution. The result of electroporation at high voltages is shown in FIG. 7A, where punctuate fluorescence is observed in the exo-nuclear cytoplasmic region, but not in the nuclear region which contains a smaller number of organelles. In total, eighteen out of twenty cells electroporated in this protocol displayed a similar staining pattern, reminiscent of what is observed using an organelle-specific dye such as rhodamine 123, which labels the mitochondrial fraction of organelles. In comparison, cells electroporated at the plasma membrane threshold potential, generally displayed a diffuse fluorescence from fluorescein entrapped in the cytosol, as shown in FIG. 7B. This observation of a differential localisation of fluorescein comparing application of low and high electric field strengths is consistent with the higher breakdown potential of intracellular organelles as predicted by equation 1 given in the background part owing to their smaller dimension. It has been shown that 2.5–10 fold higher electric field strengths are required for electroporation and fusion of isolated mitochondria compared to 10-mm diameter cells. The results are also in accord with morphological observations in giant squid axons following mild, moderate, and severe electroporation protocols.

What is claimed is:

1. A method for permeabilizing a cell, comprising:
  positioning at least one microelectrode, movable in three-dimensional space, in sufficient proximity to the cell to expose the cell to a focused electric field of strength sufficient to obtain electroporation of the cell; and
  exposing the cell to the electric field, thereby permeabilizing the cell.

2. A method for selectively permeabilizing a cell in a population of cells, comprising:
  positioning at least one microelectrode, movable in three-dimensional space, in sufficient proximity to the single cell to expose the single cell to a focused electric field of strength sufficient to obtain electroporation of the single cell without electroporating other cells in the population of cells; and
  exposing the single cell to the electric field, thereby selectively permeabilizing the cell.

3. A method for selectively permeabilizing a cell structure in a cell, comprising:
  positioning at least one microelectrode, movable in three-dimensional space, in sufficient proximity to the cell structure to expose the cell structure to a focused electric field of strength sufficient to obtain electroporation of the cell structure without electroporating other structures in the cell; and
  exposing the cell to the electric field, thereby selectively permeabilizing the cell structure.

4. The method according to claim 1, 2 or 3, wherein the at least one microelectrode is controlled by a high-graduation micromanipulator.

5. The method according to claim 1, 2, or 3, wherein at least two microelectrodes are placed in proximity to the single cell and the electric field is applied between the two electrodes.

6. The method according to claim 1, 2, or 3, wherein at least two microelectrodes are placed in proximity to the cell structure and the electric field is applied between the two electrodes.

7. The method according to claim 1, 2 or 3, further comprising providing at least one mesoscopic electrode held at ground or at a negative potential.

8. The method according to claim 3, wherein the cell structure is an intracellular organelle.

9. The method according to claim 3, wherein the at least one microelectrode is placed within the cell containing the cell structure.

10. The method according to claim 1 or 2, wherein the at least one microelectrode generates a voltage at the membrane of the cell from 10 mV to 100 V.

11. The method according to claim 3, wherein the at least one microelectrode generates a voltage at the cell structure from 10 mV to 100 V.

12. The method according to claim 6, wherein the distance between the two microelectrodes is less than 10 mm.

13. The method according to claim 12, wherein the distance is less than 100 $\mu$m.

14. The method according to claim 13, wherein the distance is less than 20 µm.

15. The method according to claim 1, 2, or 3, wherein the diameter of the end is at the at least one microelectrode is less than 1 µm.

16. The method according to claim 1, 2, or 3, wherein the electric field is applied by a rectangular DC voltage pulse.

17. The method according to claim 1 or 2, further comprising contacting the cell with cell-impermeable solutes, wherein the cell-impermeable solutes are transported through pores created in the cell by the electroporation.

18. The method according to claim 3, further comprising contacting the cell structure with cell-impermeable solutes, wherein the cell-impermeable solutes are transported through pores created in the cell structure by the electroporation.

19. The method according to claim 17, wherein the solutes are comprised in an extracellular medium.

20. The method according to claims 18, wherein the solutes before the electroporation are comprised in a medium entrapped in the cell structure.

21. The method according to claim 17, wherein the solutes comprise a pharmaceutically active compound.

22. The method according to claim 18, wherein the solutes comprise a pharmaceutically active compound.

23. The method according to claim 17, wherein the medium comprising the solutes is delivered to the cell by use of a catheter.

24. The method according to claim 1, 2, or 3, wherein at least one microelectrode is a carbon fiber electrode.

25. The method according to claim 1, 2, or 3, wherein at least one microelectrode comprises a hollow electrolyte-filled capillary.

26. The method according to claim 25, wherein a medium comprising cell impermeable solutes is delivered through the hollow electrolyte-filled capillary.

27. The method according to claim 25, wherein the electrolyte comprises a physiological buffer.

28. The method according to claim 17, wherein solutes are delivered to the cell by electrophoresis or electroosmosis.

29. The method according to claim 18, wherein solutes are delivered to the cell structure by electrophoresis or electroosmosis.

30. A method according to claim 25, wherein the hollow electrolyte-filled capillary comprises a fused silica capillary.

31. The method according to claim 30, wherein the fused silica capillary comprises a conductive tip.

32. The method according to claim 25, wherein the capillary comprises a tapered tip.

33. The method according to claim 31, wherein the capillary comprises a tapered tip.

34. The method according to claim 21, wherein the pharmaceutically active compound is a drug.

35. The method according to claim 22, wherein the pharmaceutically active compound is a drug.

36. The method according to claim 21, wherein the pharmaceutically active compound is a nucleic acid.

37. The method according to claim 22, wherein the pharmaceutically active compound is a nucleic acid.

38. The method according to claim 1 or 2, wherein a biological marker or dye is transported into the cell when the cell is permeabilized.

39. The method according to claim 3, wherein a biological marker or dye is transported into the cell structure when the cell structure is permeabilized.

40. The method according to claim 1 or 2, wherein a nanoparticle is transported into the cell when the cell is permeabilized.

41. The method according to claim 3, wherein a nanoparticle is transported into the cell structure when the cell is permeabilized.

42. The method according to claim 8, wherein the organelle is a cell nucleus or mitochondria.

43. The method according to claim 1, 2, or 3, further comprising the step of detecting a cellular response as a result of the electroporation.

44. The method according to claim 43, wherein the cellular response is a change in levels of intracellular calcium.

45. The method according to claim 44, further comprising providing to the cell a fluorogenic calcium chelating dye.

46. The method according to claim 17, wherein the solutes are chemically separated prior to contacting the cell.

47. The method according to claim 18, wherein the solutes are chemically separated prior to contacting the cell structure.

48. The method according to claim 46, wherein the separation occurs in the at least one microelectrode.

49. The method according to claim 47, wherein the separation occurs in the at least one microelectrode.

50. The method according to claim 1, 2, or 3, wherein the cell is a tumor cell.

51. The method according to claim 1, 2, or 3, wherein the cell is a neuron.

52. The method according to claim 51, wherein the cell is from a patient with a neurodegenerative disease.

53. The method according to claim 51, wherein the neuron is a neuron in the Nigrostriatal pathway.

54. The method according to claim 1, 2, or 3, wherein the at least one microelectrode is positioned by use of device selected from the group consisting of: a microscope, at least one micropositioner, and a stereotactic device.

55. A method for delivering an impermeable solute inside a cell structure, comprising:

contacting an isolated cell structure with a medium comprising the impermeable solute;

positioning at least one microelectrode, movable in three-dimensional space, in sufficient proximity to the isolated cell structure to expose the structure to a focused electric field of strength sufficient to generate pores in the cell structure, wherein the solute is transferred into the cell structure; and sealing the pores.

56. The method according to claim 55, wherein the cell structure is a liposome, cell nucleus, or mitochondria.

57. A method for introducing a cell-impermeable solute into one or more cells cell, comprising:

providing at least one liquid-filled capillary, movable in three-dimensional space and capable of delivering a current through the liquid in the capillary;

positioning the liquid-filled capillary in proximity to the one or more cells in a solution, wherein either the liquid in the capillary or the solution comprises a cell-impermeable solute;

delivering a current through the liquid in the capillary to the one or more cells, thereby exposing the one or more cells to an electric field of strength sufficient to permeabilize the one or more cells and to introduce the cell-impermeable solute into the cell.

58. The method according to claim 57, wherein the at least one capillary is positioned using a high-graduation micromanipulator.

59. The method according to claim 57, further comprising selectively electroporating a cell structure within one of the one or more cells.

60. The method according to claim 59, wherein the cell structure is an intracellular organelle.

61. The method according to claim 59, wherein the at least one capillary comprises a tip and the tip is placed within the cell comprising the cell structure.

62. The method according to claim 57, wherein the at least one capillary generates a voltage at the membrane of the cell from 10 mV to 100 V.

63. The method according to claim 59, wherein the at least one capillary generates a voltage at the cell structure from 10 mV to 100 V.

64. The method according to claim 57, wherein the electric field is applied by a rectangular DC voltage pulse.

65. The method according to claim 57, wherein the solutes comprise a pharmaceutically active compound.

66. The method according to claim 57, wherein the liquid comprises an electrolyte.

67. The method according to claim 66, wherein the electrolyte comprises a physiological buffer.

68. The method according to claim 57, wherein solutes are delivered to the cell by electrophoresis or electroosmosis.

69. A method according to claim 57, wherein the capillary comprises a fused silica capillary.

70. The method according to claim 57, wherein the fused silica capillary comprises a conductive tip.

71. The method according to claim 57, wherein capillary comprises a tapered tip.

72. The method according to claim 61, wherein the pharmaceutically active compound is a drug.

73. The method according to claim 61, wherein the pharmaceutically active compound is a nucleic acid.

74. The method according to claim 57, wherein a biological marker or dye is transported into the cell when the cell is permeabilized.

75. The method according to claim 57, wherein a nanoparticle is transported into the cell when the cell is permeabilized.

76. The method according to claim 60, wherein the organelle is a cell nucleus or mitochondria.

77. The method according to claim 57, further comprising the step of detecting a cellular response after introduction of the solute.

78. The method according to claim 77, wherein the cellular response is a change in levels of intracellular calcium.

79. The method according to claim 78, further comprising providing to the cell a fluorogenic calcium chelating dye.

80. The method according to claim 57, wherein the solutes are chemically separated prior to contacting the cell.

81. The method according to claim 80, wherein the separation occurs within the capillary.

82. The method according to claim 57, wherein at least one of the one or more cells is a tumor cell.

83. The method according to claim 57, wherein at least one of the one or more cells is a neuron.

84. The method according to claim 83, wherein the at least one cell is from a patient with a neurodegenerative disease.

85. The method according to claim 83, wherein the neuron is a neuron in the Nigrostriatal pathway.

86. The method according to claim 57, wherein the capillary is positioned by use of device selected from the group consisting of: a microscope, at least one micropositioner, and a stereotactic device.

* * * * *